United States Patent
Pigott

(10) Patent No.: US 10,117,735 B2
(45) Date of Patent: Nov. 6, 2018

(54) BIODEGRADABLE INTRAVASCULAR FILTER

(71) Applicant: Promedica Health System, Inc., Toledo, OH (US)

(72) Inventor: John P. Pigott, Sylvania, OH (US)

(73) Assignee: PROMEDICA HEALTH SYSTEM, INC., Toledo, OH (US)

( * ) Notice: Subject to any disclaimer, the term of this patent is extended or adjusted under 35 U.S.C. 154(b) by 302 days.

(21) Appl. No.: 14/654,683

(22) PCT Filed: Dec. 19, 2013

(86) PCT No.: PCT/US2013/076467
§ 371 (c)(1),
(2) Date: Jun. 22, 2015

(87) PCT Pub. No.: WO2014/100375
PCT Pub. Date: Jun. 26, 2014

(65) Prior Publication Data
US 2015/0351894 A1 Dec. 10, 2015

Related U.S. Application Data

(60) Provisional application No. 61/739,897, filed on Dec. 20, 2012.

(51) Int. Cl.
*A61F 2/01* (2006.01)

(52) U.S. Cl.
CPC .......... *A61F 2/01* (2013.01); *A61F 2002/016* (2013.01); *A61F 2210/0004* (2013.01); *A61F 2250/003* (2013.01)

(58) Field of Classification Search
CPC .................. A61F 2/01; A61F 2250/003; A61F 2002/016; A61F 2210/004
See application file for complete search history.

(56) References Cited

U.S. PATENT DOCUMENTS

| | | | |
|---|---|---|---|
| 5,375,612 A | 12/1994 | Cottenceau et al. | |
| 6,443,972 B1 | 9/2002 | Bosma et al. | |
| 2004/0059373 A1* | 3/2004 | Shapiro | A61F 2/01 606/200 |
| 2006/0020286 A1 | 1/2006 | Niermann | |
| 2006/0025852 A1* | 2/2006 | Armstrong | A61B 17/12022 623/1.17 |
| 2007/0156231 A1 | 7/2007 | Weber | |

FOREIGN PATENT DOCUMENTS

| | | |
|---|---|---|
| WO | 0222048 A2 | 3/2002 |
| WO | 2012118696 A1 | 9/2012 |

* cited by examiner

*Primary Examiner* — Todd Scherbel
*Assistant Examiner* — Christina Lauer
(74) *Attorney, Agent, or Firm* — Standley Law Group LLP

(57) ABSTRACT

An intravascular filter (10) has a main filter portion (12) and an anchor portion (14). The main filter portion is made up of a number of struts (16), which form a first and a second biodegradable filter sections (26,28). The first and the second biodegradable filter sections biodegrade at different rates. The anchor portion secures the filter within a blood vessel and also has a collar (32). The first and the second biodegradable portions may have a different thickness and may be comprised of different materials. The collar may be formed from a resiliently deformable material.

8 Claims, 4 Drawing Sheets

BIODEGRADABLE INTRAVASCULAR FILTER

BACKGROUND OF THE INVENTION

This invention relates in general to filters for use in blood vessels. In particular, this invention relates to an improved structure for an intravascular filter that includes at least two biodegradable filter sections that degrade at different rates.

An embolism is a detached intravascular mass that is carried by circulation through blood vessels in a living body and that is capable of clogging a vessel that is too small to let it pass therethrough. When this happens, the flow of blood through the vessel is undesirably stopped by the embolus. In many instances, an embolus is a small piece of a blood clot that breaks off from a site of trauma or other injury and travels to another site in the living body.

One type of embolism is a pulmonary embolism, which is a blockage in a lung artery by an embolus. A pulmonary embolism can cause damage to lung tissue from the obstruction of blood flow. Further, low oxygen blood levels may be caused by the pulmonary embolism, which may cause damage to other organs due to oxygen deprivation. If the pulmonary embolism is severe enough, it may even result in death. A pulmonary embolism is one of the more common causes of death in people who remain in bed for a long time. In most cases, a pulmonary embolism is a complication of a condition called deep vein thrombosis (DVT). In DVT, blood clots form in the deep veins of the body, most often in the legs. These clots can break free and travel to the lung, causing the pulmonary embolism.

Intravascular filters are well known devices that are used to restrain emboli from traveling throughout a living body. Typically, these intravascular filters are inserted within a blood vessel in order to restrain the emboli from traveling therethrough until the normal processes of the body are capable of partially or fully dissolving them. The inferior vena cava (IVC) is a large vein that returns blood from the lower half of the body to the heart. In many instances, the IVC is a desirable location for placement of an intravascular filter. Intravascular filters are generally inserted within the IVC in patients at risk for DVT and who cannot undergo standard anticoagulation therapy (or in patients where anticoagulation therapy is not effective). As the delivery system profile of these intravascular filters has decreased and the ease of inserting same improved, more of such filters are being utilized. This is especially true with patients who have multiple trauma or major orthopedic procedures.

Until recently, most intravascular filters were permanent type filters, meaning that even though the need for protection from pulmonary emboli was relatively short (measured in days to months), the intravascular filter was simply left in the patient after the need for protection had passed. This was because the intravascular filter could only be removed with another relatively major surgical operation. Thus, the risk of removing the filter was greater than the risk of leaving the filter in place. Consequently, rather than subjecting the patient to a second operation, the intravascular filter is often simply left in the patient after the need for protection had passed.

More recently, however, recoverable intravascular filters have been developed. Such recoverable intravascular filters can be removed when the need for protection ends using a less invasive procedure than previously known. Furthermore, it is known to provide intravascular filters that include some bio-absorbable components, wherein at least a portion of these filters will be broken down and absorbed by the body over time. This allows for protection from a pulmonary embolism for a period of time without requiring recovery of at least a portion of the filter. Such a filter is described in U.S. Pat. No. 5,375,612 to Cottenceau et al. However, risks are still presented by the use of such procedures and devices. Thus, it would be desirable to provide an improved structure for a intravascular filter that addresses these issues.

SUMMARY OF THE INVENTION

This invention relates to an intravascular filter that includes a biodegradable main filter portion, wherein the main filter portion will be broken down over time and be absorbed by or passed out of the body. The intravascular filter includes a main filter portion having at least first and second biodegradable filter sections that degrade at different rates.

Various advantages of this invention will become apparent to those skilled in the art from the following detailed description of the preferred embodiments, when read in light of the accompanying drawings.

DETAILED DESCRIPTION OF THE PREFERRED EMBODIMENTS

Figure 1:
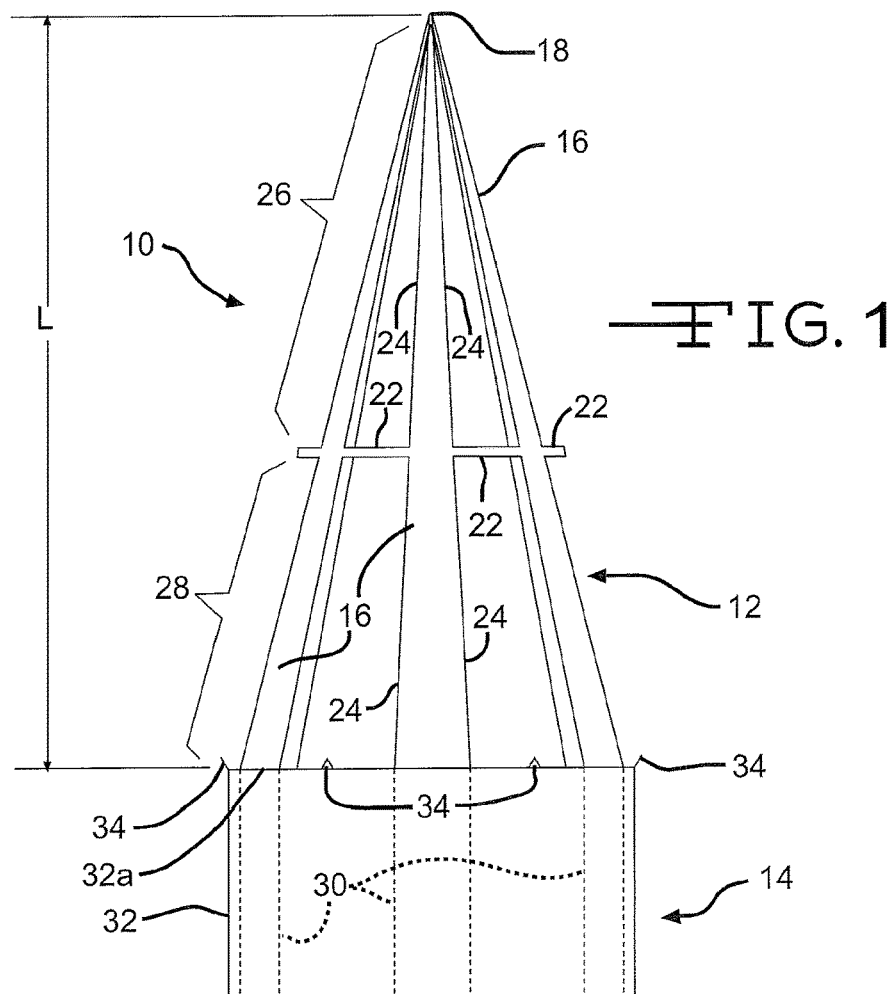
FIG. 1 is a side elevational view of an intravascular filter according to a first embodiment of this invention.
Figure 2:
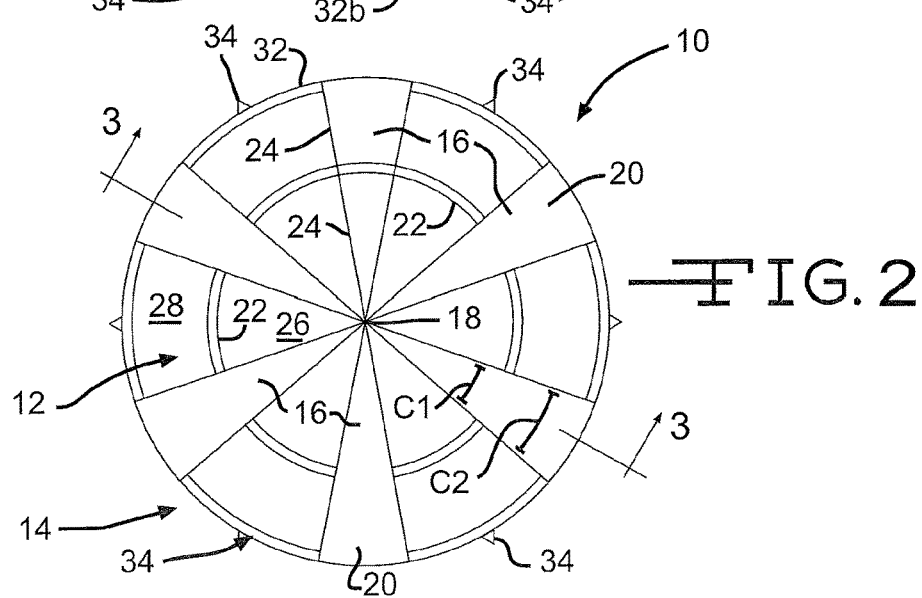
FIG. 2 is a top plan view of the intravascular filter illustrated in FIG. 1.
Figure 3:
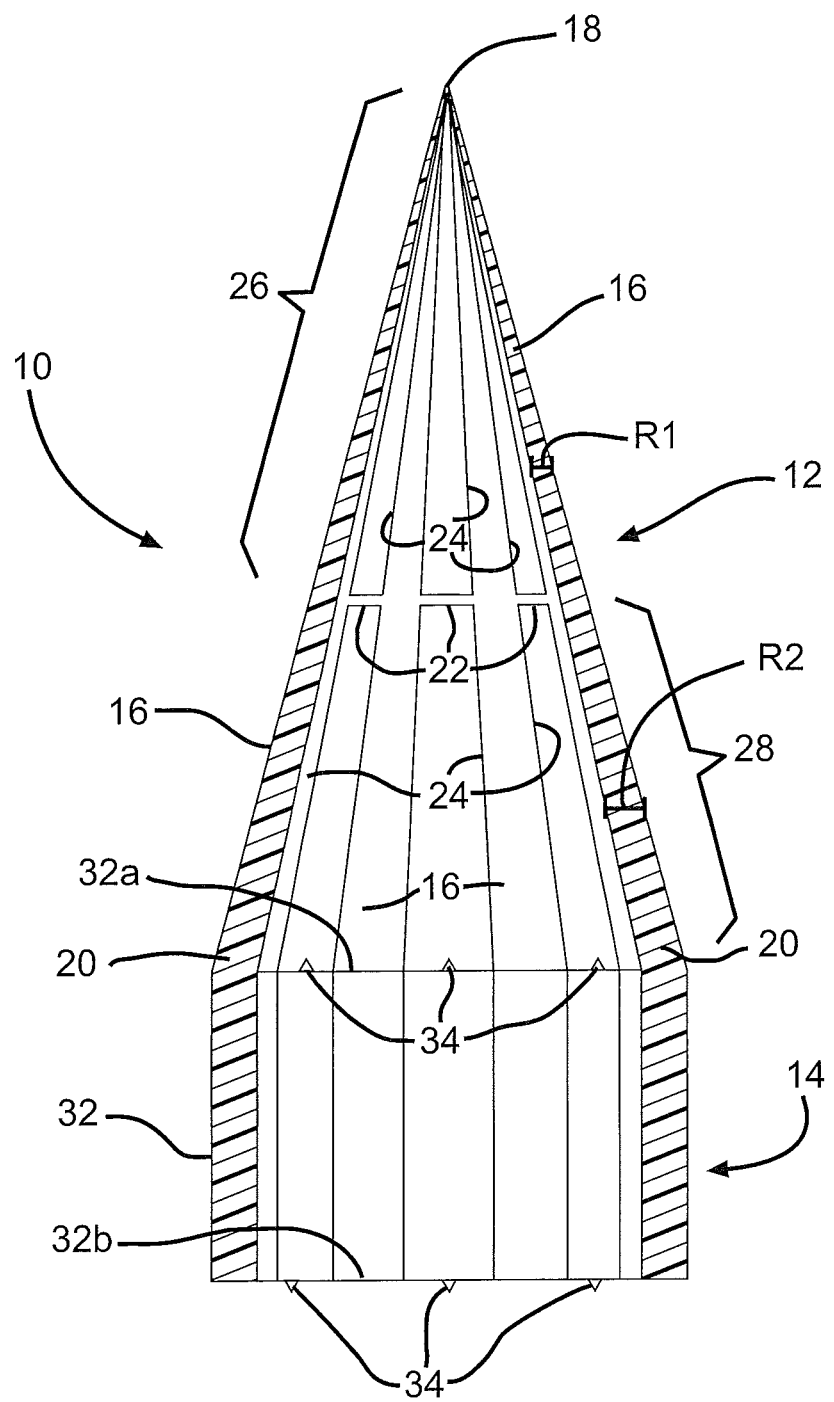
FIG. 3 is a sectional elevational view of the intravascular filter taken along line 3-3 of FIG. 2.

Referring now to the drawings, there is illustrated in FIGS. 1 through 3 a first embodiment of an intravascular filter, indicated generally at 10, in accordance with this invention. The filter 10 includes a first or main filter portion, indicated generally at 12, and a second or anchor portion, indicated generally at 14.

In the illustrated embodiment, the main filter portion 12 includes a plurality of individual, spaced apart struts 16 that each extend from an apex 18 of the main filter portion 12 to a base 20 thereof. The main filter portion 12 defines a length L that extends from the apex 18 to the base 20, as indicated in FIG. 1. In the illustrated embodiment, each strut 16 has a circumferential width that increases from the apex 18 to the base 20. This is illustrated in FIG. 2 by a first circumferential width C1 between the apex 18 and the base 20 and a second circumferential width C2 between the first circumferential width C1 and the base 20, wherein the second circumferential width C2 is larger than the first circumferential width C1. In the illustrated embodiment, each strut 16 also has a radial thickness that increases from the apex 18 to the base 20. This is best illustrated in FIG. 3 by a first radial thickness R1 between the apex 18 and the base 20 and a second radial thickness R2 between the first radial thickness R1 and the base 20, wherein the second radial thickness R2 is larger than the first radial thickness R1. Thus, in the illustrated embodiment, each of the struts 16 has an increasing cross-sectional area (i.e., the two dimensional region across the strut 16) and an increasing cross-sectional perimeter (i.e., the two dimensional border around the cross-sectional area) as the strut 16 extends from the apex 18 to the base 20 thereof. However, the struts 16 may have any other desired shapes or sizes. For example, while the geometry of the struts 16 have been described in terms of polygons with width and thick and perimeter, it must be understood that the struts may have any suitable geometry, such as a conical section (e.g. circular or oval with a radial dimension and a circumference) or any other suitable geometry.

In the illustrated embodiment, the main filter portion 12 includes a plurality of optional cross members 22 that, together with the struts 16, defines a plurality of apertures 24 extending through the main filter portion 12. The number and position of the cross members 22 may be varied as desired to vary the size and shape of the apertures 24. Additionally, the cross members 22 can provide additional support between the struts 16. However, the construction of the cross members 22 may be other than illustrated, if so desired. Also, it will be appreciated that the main filter portion 12 need not have any cross members 22, and further that the apertures 24 may be defined by varying the geometry of the struts 16. For example, the struts 16 may extend in an alternating zigzag pattern or any other desired pattern.

In the illustrated embodiment, the main filter portion 12 includes a first section 26 (which extends from the apex 18 to about mid-way between the apex 18 and the base 20) and a second section 28 (which extends from about mid-way between the apex 18 and the base 20 to the base 20). However, the structures of the first section 26 and the second section 28 may be other than illustrated, if so desired. In the illustrated embodiment, the first section 26 is preferably formed from a first biodegradable polymer or other material and the second section 28 is preferably formed from of a second biodegradable polymer or other material that is different from the first biodegradable polymer or other material. In the illustrated embodiment, the material used to form the first section 26 preferably degrades at a faster rate than the material used to form the second section 28, for a purpose to be discussed below.

In the illustrated embodiment, the main filter portion 12 is integrally formed with the anchor portion 14. Alternatively, however, the main filter portion 12 may be formed separately from the anchor portion 14 and secured thereto by any suitable mechanism, such as chemical bonding, adhesion, mechanical fastening, or any other desired mechanism. Alternatively, the main filter portion 12 and the anchor portion 14 may be other than illustrated, if so desired.

In the illustrated embodiment, the anchor portion 14 preferably includes a collar 32. The collar 32 is preferably resiliently deformable to allow for compact insertion into and subsequent expansion within a blood vessel, such as the IVC. The anchor portion 14 may be also be formed from a biodegradable material, such as the material used to form either of the first or second sections 26 and 28, or any other desired biodegradable material. Preferably, the material used to form the anchor portion 14 degrades a rate slower than the materials used to form the main filter portion 12, although such is not required. Alternately, the anchor portion 14 may be formed from a non-biodegradable material, if desired.

In the illustrated embodiment, a plurality of optional barbs 34 is provided about the circumference of the collar 32 at both a first end 32a thereof and a second collar end 32b thereof. The barbs 34 can be provided to engage the interior wall of a blood vessel to anchor the intravascular filter 10 within the blood vessel. The barbs 34 may be formed from the same material as the rest of the collar 32, although any suitable polymer, metallic, or other material may be used if desired.

As discussed above, the first section 26 is preferably formed from a first biodegradable polymer or other material and the second section 28 is formed from a different second biodegradable polymer or other material. Alternatively, the first section 26 and the second section 28 of the main filter portion 12 can be formed from the same material, but having different dimensional characteristics that cause the first section 26 to biodegrade at a faster rate than the second section 28. For example, the portions of the struts in the first section 26 may be of decreased thickness or size relative to the portions of the struts in the second section 28. Alternatively, the struts 16 may have a consistent thickness or size from the apex 18 to the base 20 while still being formed from different biodegradable materials. In this case, the first section 26 degrades at a faster rate than the second section 28 because of the difference in the biodegradability of the two different materials.

The structure of the intravascular filter 10 may be other than as specifically illustrated, if so desired. For example, the main filter portion 12 may have any desired configuration including any number of cross members 22 (or no cross members at all) forming any number of apertures 24 in any desired configuration with any suitable geometry of the struts 16, so long as the main filter portion 12 has at least first and second sections that biodegrade at different rates. Also, the main filter portion 12 may have more than the illustrated two sections 26 and 28, if desired. Additionally, it should be understood that the while a difference in biodegradability has been described due to a change in thickness, it must be understood that a difference in biodegradability due to changes in geometry includes a change in width, cross-sectional area, perimeter, radius, circumference, or any other suitable geometric description of a change in configuration that changes the biodegradability.

Figure 4:
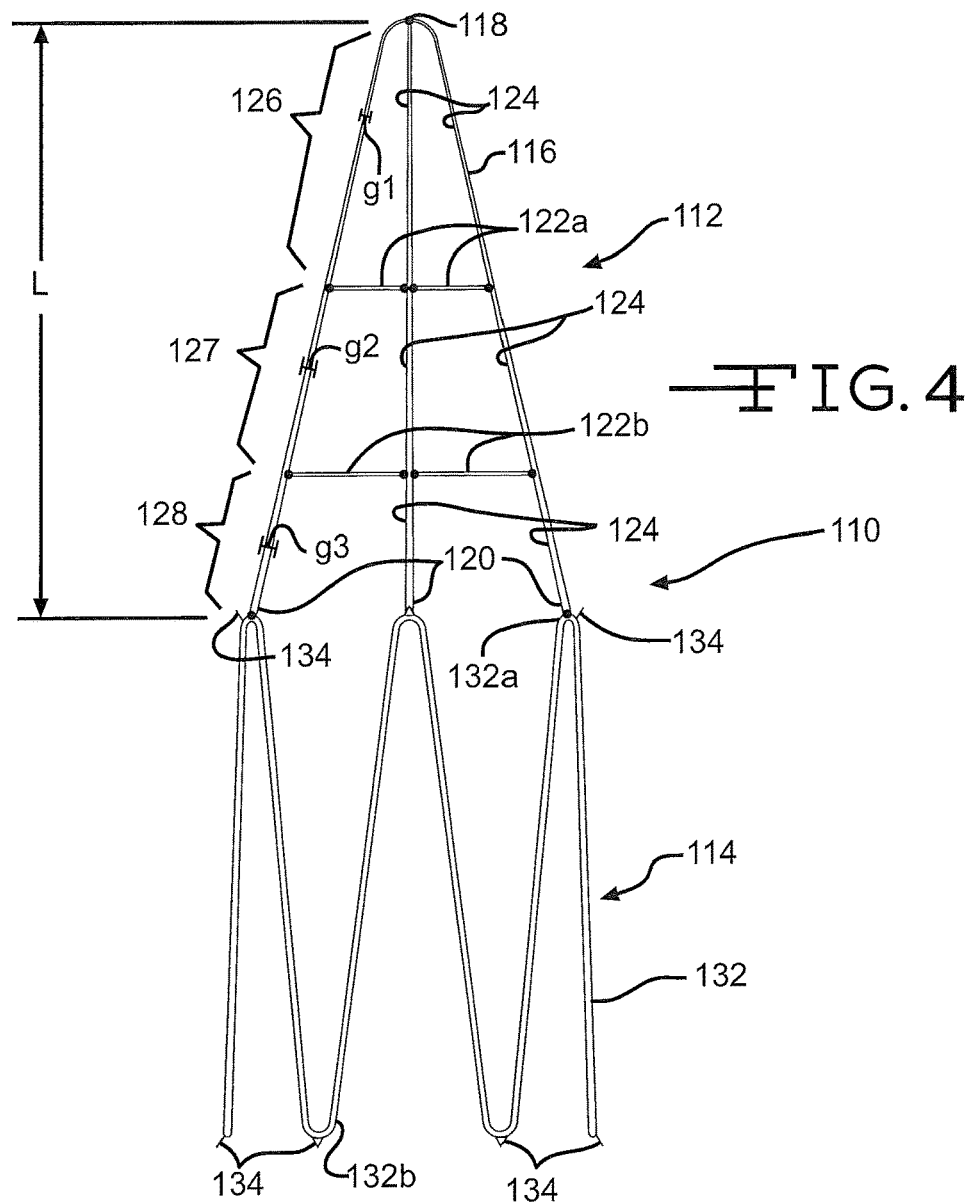
FIG. 4 is a side elevational view of an intravascular filter according to a second embodiment of this invention.
Figure 5:
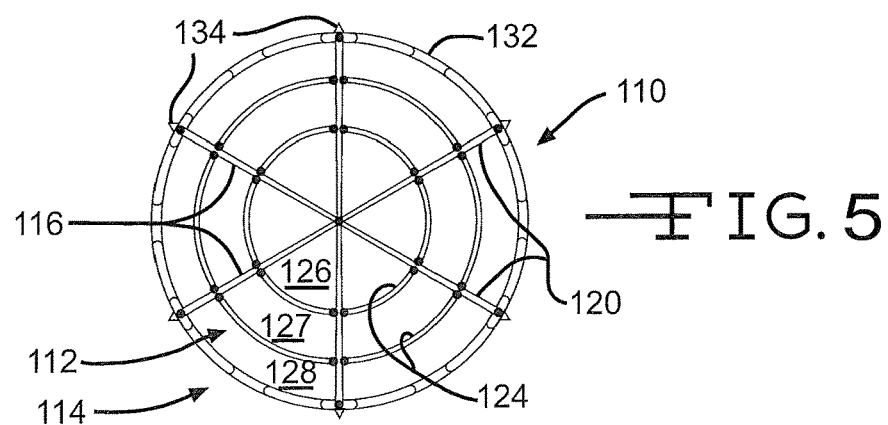
FIG. 5 is a top plan view of the intravascular filter illustrated in FIG. 4.

FIGS. 4 and 5 illustrate a second embodiment of an intravascular filter, indicated generally at 110, accordance with this invention. In this second embodiment, the intravascular filter 110 has a first or main filter portion, indicated generally at 112, including three sections 126, 127, and 128 that are formed from three different biodegradable materials. The main filter portion 112 is connected to a second or anchor portion, indicated generally at 114, that is similar to a traditional vascular filter "accordion" base.

In the illustrated embodiment, the biodegradable material is a biodegradable suture material that forms a plurality of individual, spaced apart struts 116 extending from an apex 118 to a base 120 thereof. The main filter portion 112 defines a length L that extends from the apex 118 to the base 120, as indicated in FIG. 4. In the illustrated embodiment, the materials used to form each of the sections 126, 127, and 128 have respective thicknesses or gauges g1, g2, and g3. In the illustrated embodiment, the gauge g1 is less than the gauge g2, and the gauge g2 is less than the gauge g3. Thus, in the illustrated embodiment, each of the struts 116 has an increasing cross-sectional area and an increasing cross-sectional perimeter as the strut 116 extends from the apex 110 to the base 120 thereof. However, the construction of the struts 116 may be other than illustrated, if so desired.

In the illustrated embodiment, the main filter portion 112 includes a first plurality of optional cross members 122a and a second plurality of optional cross members 122b. Together with the struts 116, the first and second pluralities of cross members 122b define a plurality of apertures 124 extending through the main filter portion 112. The number and position of the cross members 122a and 122b may be varied as desired to vary the size and shape of the apertures 124. Additionally, the cross members 122a and 122b provide additional support between the struts 116. It should be understood that the first and second cross members 122a and 122b may be formed from similar materials of similar gauges or of different materials and/or of different gauges, depending upon whether or not such cross members 122a and 122b are desired to degrade at the same rate. For example, the first and second cross members 122a and 122b may be formed from the same biodegradable suture material as the first, second, or third sections 126, 127, or 128 or from any other suitable material. Alternatively, the construction of the first, second, and third sections 126, 127, and 128 and the cross members 122a and 122b may be other than illustrated, if so desired.

It should also be understood that the main filter portion 112 need not have any cross members 122a or 122b, and further that the apertures 124 may be defined by connecting the struts 116 at various points, for example, to form an alternating zigzag pattern or any other suitable pattern desired, if so desired.

In the illustrated embodiment, the first, second, and third sections 126, 127, and 128 of the main filter portion 112 are formed from different biodegradable suture materials and different gauges so that the first section 126 degrades at a faster rate than the second section 127 and the second section 127 degrades at a faster rate than the third section 128. However, the construction of the first, second, and third sections 126, 127, and 128 may be other than illustrated, if so desired.

In the illustrated embodiment, all of the sutures that make up the main filter portion 112 may be connected to each other and to the anchor portion 114 by any suitable mechanism, such as chemical bonding, adhesion, mechanical fastening, knotting, or any other desired mechanism. Alternatively, the construction of the filter 110 may be other than illustrated, if so desired.

In the illustrated embodiment, the anchor portion 114 preferably includes a continuous spring wire 132. The wire 132 is resiliently deformable to allow for compact insertion into and subsequent expansion within a blood vessel, such as the IVC. The anchor portion 114 may be formed from a biodegradable material, such as a biodegradable metal or any other desired biodegradable material. Preferably, the anchor portion 114 degrades a rate slower than the main filter portion 112, although such is not required. Alternately, the anchor portion 114 may be formed from a non-biodegradable material, if desired.

In the illustrated embodiment, a plurality of barbs 134 is provided about the circumference of the wire 132 at a first end 132a and a second end 132b thereof. The barbs 134 are provided to engage the interior wall of a blood vessel to anchor the intravascular filter 110 within the blood vessel. The barbs 134 may be formed from the same material as the spring wire 132, a suitable polymer, metallic, or any other material if desired.

Alternatively, the first, second, and third sections 126, 127, and 128 can be formed from a single common biodegradable suture material. In this instance, the first section 126 can degrade at a faster rate than the second section 127, and the second section can degrade at a faster rate than the third section 128 due to the decreased thickness or gauge of the associated strut 116 toward the apex 118 as compared to their thickness or gauge toward the base 120.

Also, the first, second, and third sections 126, 127, and 128 can have a consistent thickness or gauge from the apex 118 to the base 120, while still being formed from different biodegradable suture materials. In this case, the first section 126 can degrade at a faster rate than the second section 127, and the second section can degrade at a faster rate than the third section 128 due to the difference in the biodegradability of the three different suture materials.

Alternatively, the construction of the filter 110 may be other than illustrated, if so desired. Additionally, it should be understood that the main filter portion 112 may have any desired configuration including any number of cross members 122a or 122b, or no cross members at all, forming any number of apertures 124 in any desired configuration with any suitable geometry of the struts 116, so long as the main filter portion 112 has at least two sections that degrade at different rates.

Figure 6:
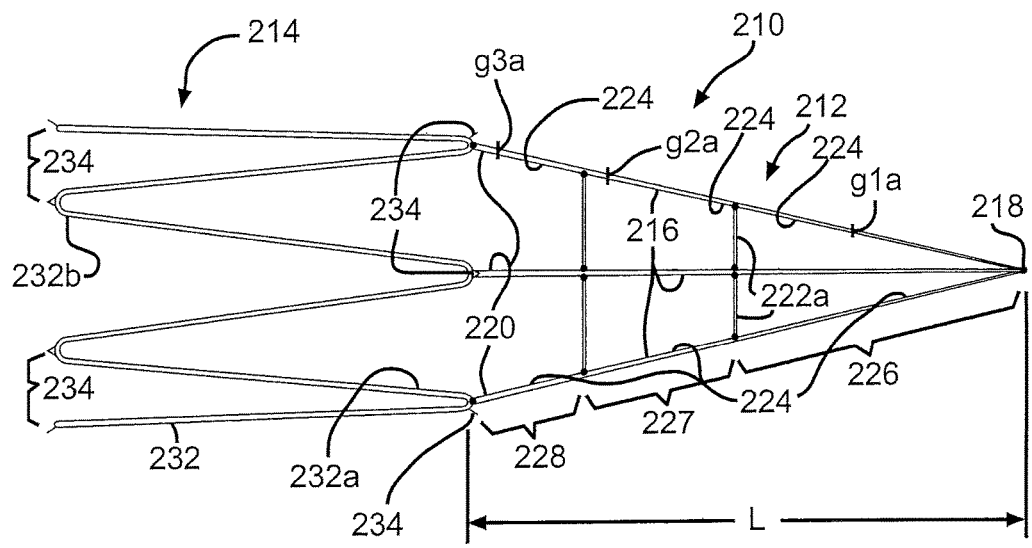
FIG. 6 is a side elevational view of an intravascular filter according to a third embodiment of this invention.

FIG. 6 illustrates a third embodiment of an intravascular filter, indicated generally at 210, that includes a first or main filter portion 212 formed from three sections 226, 227, 228 of biodegradable metal wire and a second or anchor portion, indicated generally at 214, that is similar to a traditional vascular filter "accordion" base. In this embodiment, the biodegradable wires form a plurality of individual, spaced apart struts 216 extending from an apex 218 to a base 220 thereof. The main filter portion 212 defines a length L that extends from the apex 218 to the base 220, as indicated in FIG. 6. In the illustrated embodiment, the material making up each section 226, 227, and 228 has a respective thickness or gauge g1a, g2a, and g3a. In the illustrated embodiment, the gauge g1a is less than the gauge g2a, and the gauge g2a is less than the gauge g3a. Thus, in the illustrated embodiment, each of the struts 216 has an increasing cross-sectional area and an increasing cross-sectional perimeter as the strut 216 extends from the apex 210 to the base 220 thereof. Alternatively, the construction of the struts 116 may be other than illustrated, if so desired.

In the illustrated embodiment, the main filter portion 212 includes first and second pluralities of optional cross members 222a. Together with the struts 216, the first and second pluralities of optional cross members 222b define a plurality of apertures 224. The number and position of the cross members 222a and 222b may be varied as desired to vary the size and shape of the apertures 224. Additionally, the cross members 222a and 222b provide additional support between the struts 216. It should be understood that the first and second cross members 222a and 222b may be formed from similar material of similar gauge or of different material and/or of different gauge depend upon whether or not such cross members 222a and 222b are desired to degrade at the same rate. For example, the first and second cross members 222a and 222b may be formed from the same suture material as the first, second, or third sections 226, 227, or 228, or any other suitable material. Alternatively, the construction of the first, second, and third sections 126, 127, and 128 and the cross members 122a and 122b may be other than illustrated, if so desired.

It should also be understood that the main filter portion 212 need not have any cross members 222a or 222b, and further that the apertures 224 may be defined by connecting the struts 216 at various points, for example, to form an alternating zigzag pattern or any other suitable pattern desired, if so desired.

In the illustrated embodiment, the first, second, and third sections 226, 227, and 228 of the main filter portion 212 are formed from different suture material and different gauge, where the first section 226 degrades at a faster rate than the second section 227, and the second section 227 degrades at a faster rate than the third section 228. Alternatively, the construction of the first, second, and third sections 226, 227, and 228 may be other than illustrated, if so desired.

In the illustrated embodiment, all of the wires that make up the main filter portion 212 may be connected to each other and the anchor portion 214 by any suitable mechanism, such as chemical bonding, adhesion, mechanical fastening, or any other desired mechanism. Alternatively, the construction of the filter 210 may be other than illustrated, if so desired.

In the illustrated embodiment, the anchor portion 214 preferably includes a continuous spring wire 232. The wire 232 is resiliently deformable to allow for compact insertion into and subsequent expansion within a blood vessel, such as the IVC. The cross members 222a and 222b can resiliently bend to accommodate the insertion of the filter 210 into the blood vessel.

The anchor portion 214 may be formed from a biodegradable material, such as a biodegradable metal or any other desired biodegradable material. Preferably, the anchor portion 214 degrades a rate slower than the main filter portion 212, although such is not required. Alternately, the anchor portion 214 may be formed from a non-biodegradable material, if desired.

In the illustrated embodiment, a series of barbs 234 are provided about the circumference of the wire 232 at a first end 232a and a second end 232b thereof. The barbs 234 are provided to engage the interior wall of a blood vessel to anchor the filter 210 within the blood vessel. The barbs 234 may be formed from the same material as the spring wire 232, any suitable polymer, metallic, or other material if desired.

Alternatively, the first, second, and third sections 226, 227, and 228 can all be formed from a single common biodegradable wire material. However, in this case, the first section 226 degrades at a faster rate than the second section 227, and the second section 227 degrades faster than the third section 228, due to the decreased thickness or gauge of the associated strut 216 toward the apex 218 as compared to their thickness or gauge toward the base 220.

Also, the first, second, and third sections 226, 227, and 228 can have a consistent thickness or gauge from the apex 218 to the base 220 while still being formed from different biodegradable wire materials. In this case, the first section 226 degrades at a faster rate than the second section 227, and the second section 227 degrades faster than the third section 228, due to the difference in the biodegradability of the three different wire materials.

Alternatively, the construction of the filter 210 may be other than illustrated, if so desired. Additionally, it should be understood that the main filter portion 212 may have any desired configuration including any number of cross members 222a or 222b, or no cross members at all, forming any number of apertures 224 in any desired configuration with any suitable geometry of the struts 216 so long as the main filter portion 212 has at least two sections that degrade at different rates.

Figure 7:
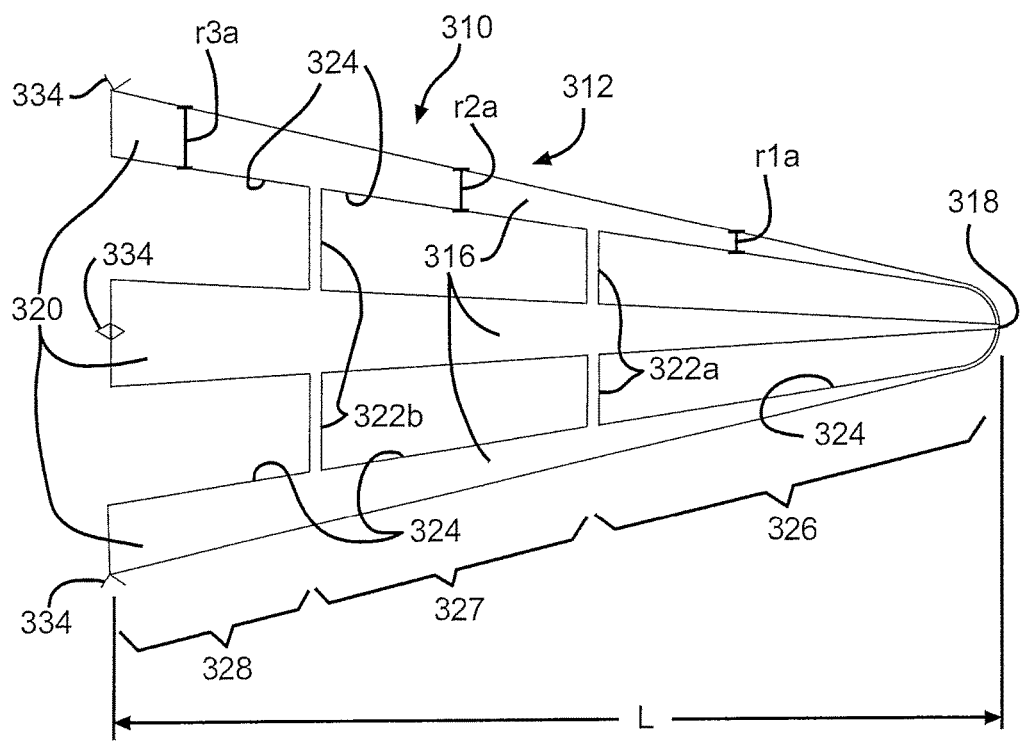
FIG. 7 is a side elevational view of an intravascular filter according to a fourth embodiment of this invention.

Referring now to FIG. 7, there is illustrated a fourth embodiment of an intravascular filter 310 formed from a single biodegradable material, such as a polymer or metal. In this embodiment, the filter 310 includes a main filter portion 312 having a plurality of individual, spaced apart struts 316 extending with increasing thickness and density from an apex 318 to a base 320 thereof. The main filter portion 312 defines a length L that extends from the apex 318 to the base 320, as indicated in FIG. 7. In the illustrated embodiment, the material making up each of the sections 326, 327, and 328 has a respective thickness r1a, r2a, and r3a increasing from the apex 318 toward the base 320. Thus, in the illustrated embodiment, each of the struts 316 has an increasing cross-sectional area and an increasing cross-sectional perimeter proceeding from the apex 310 to the base 320 thereof. Alternatively, the construction of the struts 316 may be other than illustrated, if so desired.

In the illustrated embodiment, the main filter portion 312 includes first and second pluralities of optional cross members 322a and 322b that, together with the struts 316, define a plurality of apertures 324. The number and position of the cross members 322a and 322b may be varied as desired to vary the size and shape of the apertures 224. Additionally, the cross members 322a and 322b provide additional support between the struts 316. It should be understood that the first and second cross members 322a and 322b may be formed from similar material of similar thickness or of different material and/or of different thickness, depending upon whether or not the cross member are desired to degrade at the same rate. For example, the first and second cross members 322a and 322b may be formed from the same suture material as the first, second, or third sections 326, 327, or 328, or any other suitable material. Alternatively, the construction of the main filter portion 312 may be other than illustrated, if so desired.

It will also be understood that the main filter portion 312 need not have any cross members 322a or 322b, and further that the apertures 324 may be defined by connecting the struts 316 at various points, for example, to form an alternating zigzag pattern or any other suitable pattern, if desired.

In the illustrated embodiment, the first, second, and third section 326, 327, and 328 of the main filter portion 312 are formed from different density material and different thickness, where the first section 326 degrades at a faster rate than the second section 327, and the second section 327 degrades at a faster rate than the third section 328. Alternatively, the construction of the main filter portion 312 may be other than illustrated, if so desired.

In the illustrated embodiment, all of the members that make up the main filter portion 312 may be integrally formed or may be connected to each other by any suitable mechanism, such as chemical bonding, adhesion, mechanical fastening, or any other desired mechanism. Alternatively, the construction of the main filter portion 312 may be other than illustrated, if so desired.

In the illustrated embodiment, barbs 334 extend directly from the perimeter of the base 320. Alternatively, the construction of the filter 310 may be other than illustrated, if so desired.

If desired, the first, second, and third sections 326, 327, and 328 are all formed from a single common density biodegradable material. In this situation, the first section 326 degrades at a faster rate than the second section 327, and the second section 327 degrades faster than the third section 328 due to the decreased thickness or size of the associated strut 316 toward the apex 318 as compared to their thickness or size toward the base 320.

Alternatively, the first, second, and third sections 326, 327, and 328 have a consistent thickness or size from the apex 318 to the base 320 while still being formed from different density biodegradable materials. In this case, the first section 326 degrades at a faster rate than the second section 327, and the second section 327 degrades faster than the third section 328 due to the difference in the biodegradability of the three different density materials.

Additionally, it must be understood that the main filter portion 312 may have any desired configuration including any number of cross members 322a or 322b, or no cross members at all, forming any number of apertures 324 in any desired configuration with any suitable geometry of the struts 316, so long as the main filter portion 312 has at least two sections that degrade at different rates.

Thus, with a filter according to any of the various illustrated embodiments, advantage can be taken of different absorption rates of different polymers, metals, or other biodegradable materials so that a vascular filter can be constructed with a predetermined time limit of protection from pulmonary emboli prior to degradation. In addition, materials of different degradation times and/or sections of different thicknesses of different degradation times can be utilized to allow for orderly biodegradation of the filter to prevent filter components from embolizing themselves. For example, the filter degrades from the apex to the base so that piece do not break free before sufficiently degrading.

For example, the filter can remain effective for the predetermined time necessary to prevent a pulmonary emboli under individual circumstances, but then be biodegraded and passed or bio-absorbed by the body preventing future complications. Otherwise, the filter is used in a similar fashion to current permanent and bio-absorbable filters. It is preferred that the filter be relatively low profile, as compared to other vascular devices, and be constructed of biodegradable polymer, although such is not required. Most preferably, the filter is formed of a biocompatible and absorbable polymer that is already in use in medicine, such as a known biocompatible and absorbable suture material.

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. An intravascular filter comprising:
a conically shaped main filter portion having a proximal end and a distal end and comprising a number of struts extending from an apex located at said proximal end and forming a first and a second biodegradable filter section;
an anchor portion secured to the distal end of said conically shaped main filter portion and comprising a second number of struts extending substantially in line with the struts of the main filter portion arranged in a substantially cylindrical shape; and
a collar extending about an outer surface of the second number of struts wherein said collar is shaped as a hollow cylinder;
a plurality of barbs provided about an outer surface of the collar to anchor the filter within a blood vessel, wherein at least a first portion of said barbs are located at the intersection of said collar and said main filter portion and extended towards said apex, and at least a second portion of said barbs are located at the distal end of said collar and extended away from said apex;
wherein the first biodegradable filter section and the second biodegradable filter section biodegrade at different rates.

2. The intravascular filter of claim 1 wherein:
the first biodegradable filter section comprises a first material that degrades at a first rate; and
the second biodegradable filter section comprises a second material that degrades at a second rate that is different from the first rate.

3. The intravascular filter of claim 2 wherein:
the anchor portion comprises a third material that degrades at a third rate that is different from the first rate and the second rate.

4. The intravascular filter of claim 1 wherein:
the first biodegradable filter section has a first thickness; and
the second biodegradable filter section has a second thickness that is different from the first thickness.

5. The intravascular filter of claim 1 wherein:
the first biodegradable filter section degrades before the second biodegradable filter section degrades.

6. The intravascular filter of claim 5 wherein:
the anchor portion degrades after the first and the second biodegradable filter sections degrade.

7. The intravascular filter of claim 1 wherein:
at least one of the first and second biodegradable filter sections comprises a biodegradable wire material.

8. An intravascular filter comprising:
a conically shaped main filter portion comprising a first plurality of struts extending from an apex and forming a first and a second biodegradable filter segment that have at least one of continuously increasing thickness, width, cross-sectional area, perimeter, radius, gauge, circumference and density from the first biodegradable filter section to the second biodegradable filter section;
an anchor segment comprising a second plurality of struts arranged in a substantially cylindrical shape;
a collar extending about an outer surface of the second plurality of struts and having a proximal end and a distal end; and
a plurality of barbs configured to anchor the filter within a blood vessel, wherein at least one of said barbs extends from the proximal end of said collar towards said blood vessel wall and said apex, and at least one other of said barbs extends from the distal end of said collar towards said blood vessel wall and away from said apex;
wherein the first biodegradable filter segment and the second biodegradable filter segment biodegrade at different rates.

* * * * *